(12) United States Patent
Linnosaari

(10) Patent No.: US 7,203,273 B2
(45) Date of Patent: Apr. 10, 2007

(54) SCANNING DUAL ENERGY X-RAY IMAGING

(75) Inventor: Matti Linnosaari, Helsinki (FI)

(73) Assignee: GE Healthcare Finland Oy (FI)

( * ) Notice: Subject to any disclaimer, the term of this patent is extended or adjusted under 35 U.S.C. 154(b) by 167 days.

(21) Appl. No.: 11/002,985

(22) Filed: Nov. 30, 2004

(65) Prior Publication Data
US 2006/0115049 A1    Jun. 1, 2006

(51) Int. Cl.
*A61B 6/14* (2006.01)
(52) U.S. Cl. .................... 378/39; 378/98.11; 378/98.12
(58) Field of Classification Search ................. 378/38, 378/39, 40, 98.11, 98.12
See application file for complete search history.

(56) References Cited

U.S. PATENT DOCUMENTS

| 4,963,746 A | 10/1990 | Morgan et al. | |
|---|---|---|---|
| 6,381,301 B1* | 4/2002 | Massie | 378/39 |
| 2003/0235265 A1* | 12/2003 | Clinthorne et al. | 378/4 |

* cited by examiner

*Primary Examiner*—Edward J. Glick
*Assistant Examiner*—Chih-Cheng Glen Kao
(74) *Attorney, Agent, or Firm*—Andrus, Sceales, Starke & Sawall, LLP

(57) ABSTRACT

The invention concerns a method for a dentomaxillofacial X-ray imaging. It is provided an X-ray beam (15) having a first radiation spectrum and a flat cross-sectional form towards a predetermined dentomaxillofacial area (Q) of a patient (P), and an image receptor (8) in a carrier (7) positioned outside the head of a patient. During a first exposure said X-ray beam and said carrier with the inserted image receptor are moved in a first rotational or linear direction, whereupon a first image of the dentomaxillofacial area is created on said image receptor. Then it is provided an X-ray beam having a second radiation spectrum and the flat cross-sectional form. During a second exposure said X-ray beam and said carrier with the same image receptor are moved in a second rotational or linear direction that is e.g. opposite to said first direction, whereupon a second image of the same dentomaxillofacial area is created on said image receptor. Finally the intensity values of the first image and the intensity values of the second image are subtracted from each other, whereupon a resultant image is formed, which resultant image is provided for further use.

22 Claims, 4 Drawing Sheets

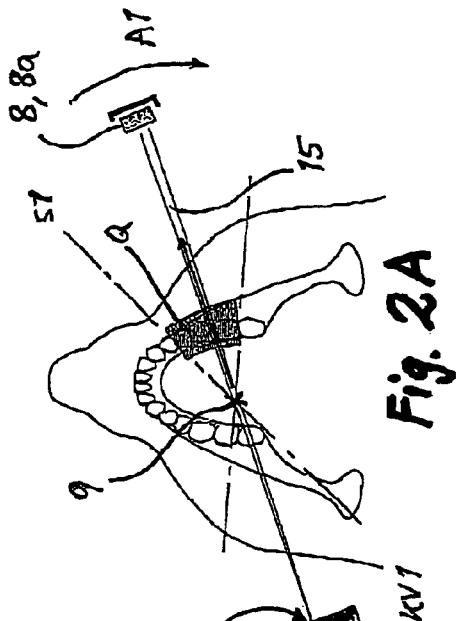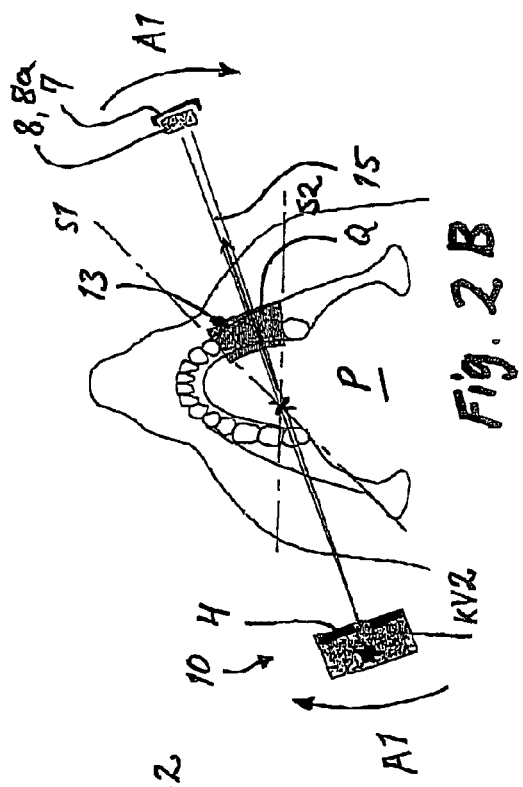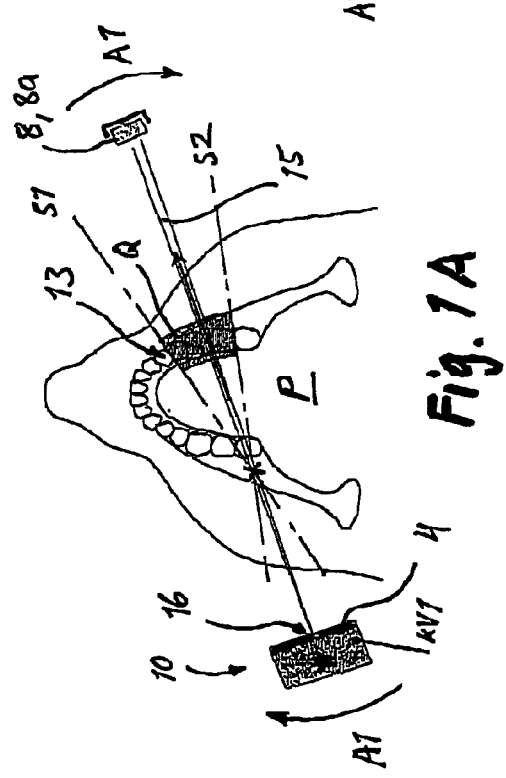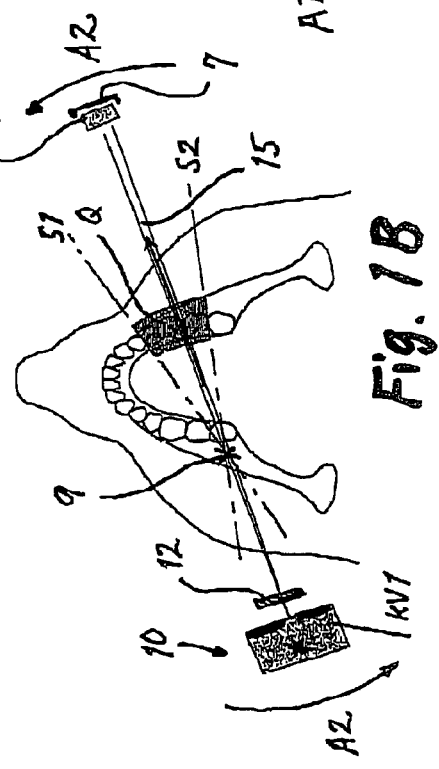

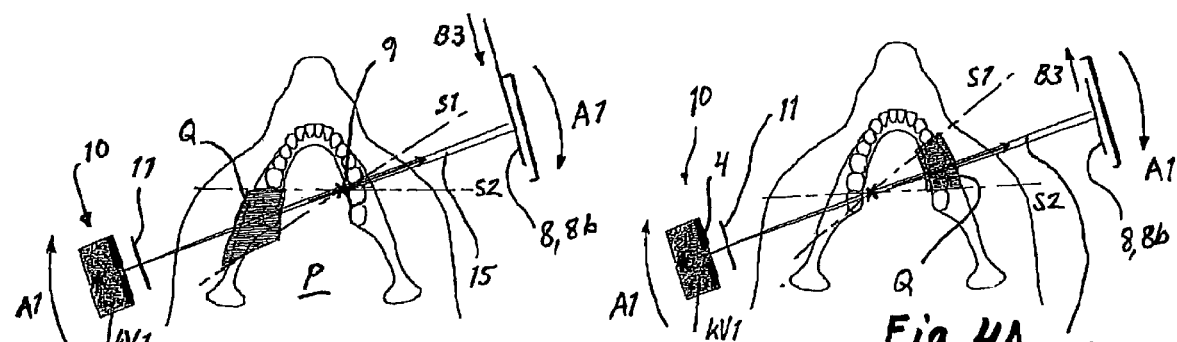

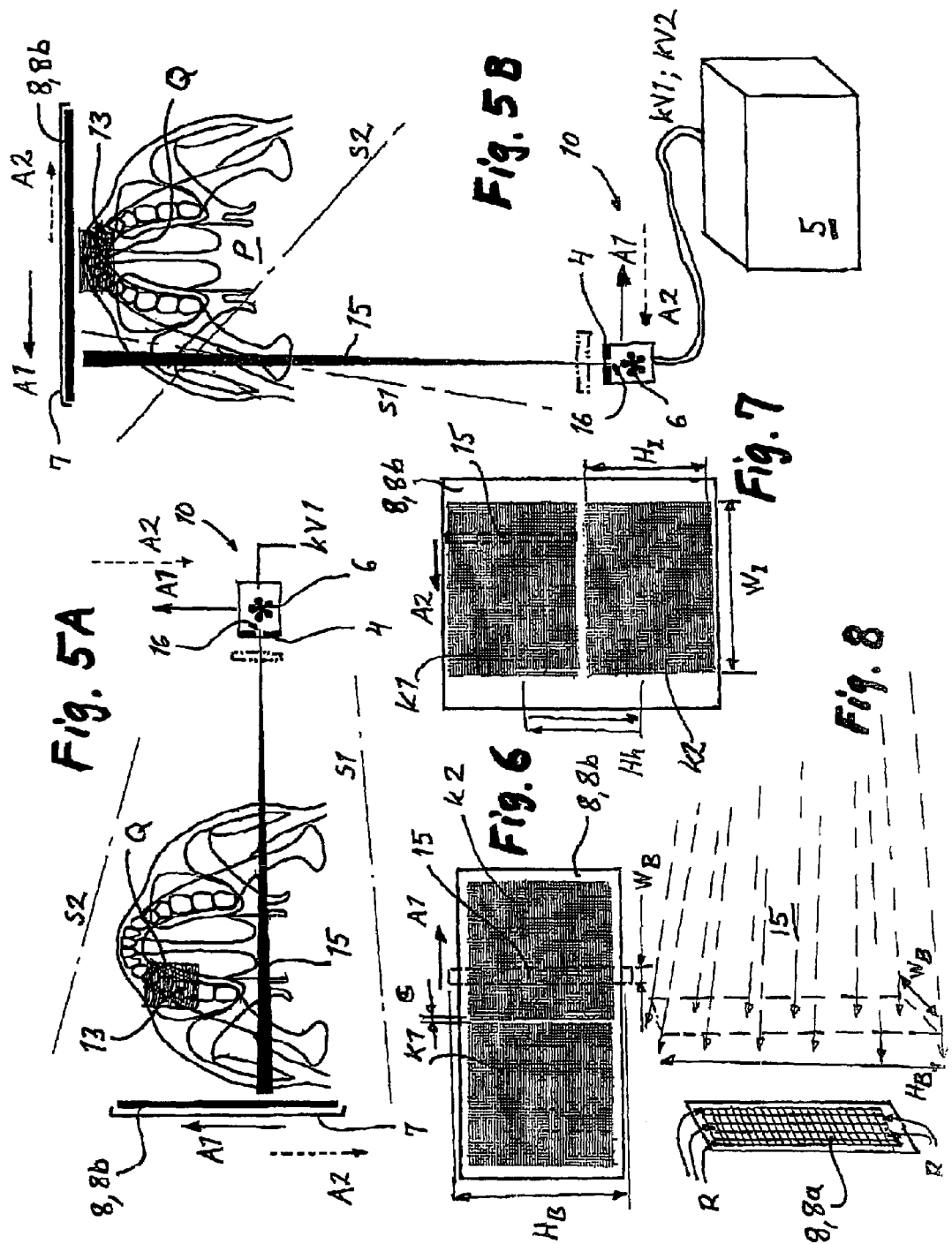

SCANNING DUAL ENERGY X-RAY IMAGING

FIELD OF THE INVENTION

The invention relates a method for a dentomaxillofacial X-ray imaging utilizing dual energy narrow beam radiography technology in subtraction mode. Here this method is used for attaining images from a dentomaxillofacial area like teeth and/or jaw and/or temporomandibular joint of the patient.

BACKGROUND OF THE INVENTION

The patent publication U.S. Pat. No. 4,963,746 discloses an energy discriminating apparatus and method for use in connection with digital radiography and fluoroscopy to search the whole body of a person. In use of the detection system and method an X-ray source is actuated to direct X-rays through a patient's body, the X-rays including both higher and lower energy radiation. A first-detector element, including a plurality of segments each segment including a phosphor coating layer and a sensor, is positioned opposite the source to receive and respond predominantly to X-rays in a lower energy range, the remaining X-rays, being generally of higher energy, passing through the first detector element. A second detector element, also including a plurality of segments, each segment including a phosphor-coating layer and a sensor, is positioned to receive and respond to the higher energy radiation passing through the first element. The sensors are coupled respectively to each detector element segment for substantially simultaneously sensing the response and spatial location, relative to the detector elements, of radiation to which each detector element respectively responds. A filter element is interposed between the first and second detectors to enhance discrimination in the energy response of the respective detector elements. Particular filter materials and detector phosphor materials and coating weights are identified which optimize the detectors performance. The sensors produce separately and simultaneously information representing patterns of relatively lower and higher energy emergent from the patient's body. Digital data processing and conversion equipment responds to the sensors to produce digital information representing each of said images, which can be digitally processed to enhance image characteristics. For this further processing the energy subtraction is suggested so that the values obtained representing the lower energy image are then subtracted from the values representing the higher energy image. Since the attenuation of the lower energy x-rays by the soft tissue in the body is approximately the same as soft tissue attenuation of the higher energy x-rays, subtraction of the lower energy image data from the higher energy image data approximately cancels out the information describing the configuration of the soft tissue. When this information has been so cancelled, substantially all that remains in the image is the representation of bone. In this manner, the contrast and visibility of the bone is substantially enhanced by energy subtraction.

SUMMARY OF THE INVENTION

In dentistry the X-ray imaging is typically used to point out caries or other abnormalities in the teeth, though abnormalities in jawbones and/or temporomandibular joints sometimes need also attention. The dentists want to see primarily the formation of the bone and teeth. The functioning of the temporomandibular joints can be of interest to the dentist, too, or to physicians in other fields of medicine. These searches are generally performed using panoramic dental imaging, whereupon these intraossicular abnormalities can be normally detected thanks to focusing possibility inherent in panoramic systems. The focusing property of the panoramic imaging greatly decreases the soft tissue shading and bone blur. Accordingly, most dentists are quite satisfied with the X-ray images attained by panoramic or linear scanning methods.

The dual energy discriminating systems are directed to search the general condition of the bones, e.g. to determine a possible osteoporosis and a state of the intervertebral discs, or detect possible fractures of the bones. With the dual energy discriminating systems the noise in the image caused the soft tissue surrounding the bones can be greatly eliminated and hence the bones can be examined as separated from other body parts.

According to the first aspect of the invention the method for a dentomaxillofacial X-ray imaging comprises: providing an X-ray beam having a first radiation spectrum and a flat cross-sectional form towards a predetermined dentomaxillofacial area of a patient; arranging an image receptor in a carrier positioned outside the head of a patient, said image receptor being transversal to said X-ray beam; while radiating said image receptor with said X-ray beam through said dentomaxillofacial area: moving said X-ray beam and said carrier with the inserted image receptor in a first rotational or linear direction, whereupon a first image of the dentomaxillofacial area is created on said image receptor, said image being constituted about first intensity values that are proportional to the radiation with said first spectrum transmitted through said dentomaxillofacial area; providing an X-ray beam having a second radiation spectrum and the flat cross-sectional form towards said predetermined dentomaxillofacial area of the patient; utilizing said image receptor arranged in said carrier outside the head of the patient; while radiating said image receptor with said X-ray beam; moving said X-ray beam and said carrier with the inserted image receptor in a second rotational or linear direction that is opposite to said first direction, whereupon a second image of the same dentomaxillofacial area is created on said image receptor, said image being constituted about second intensity values that are proportional to the radiation with said second spectrum transmitted through said dentomaxillofacial area; subtracting said first intensity values and said second intensity values from each other, whereupon a resultant image is formed; and providing the resultant image as such or after processing for further use.

According to the second aspect of the invention the method for a dentomaxillofacial X-ray imaging comprises: providing an X-ray beam having a first radiation spectrum and a flat cross-sectional form towards a predetermined dentomaxillofacial area of a patient; arranging an image receptor in a carrier positioned outside the head of a patient, said image receptor being transversal to said X-ray beam; while radiating said image receptor with said X-ray beam: moving for the first time said X-ray beam and said carrier with the inserted image receptor from a start position in a first rotational or linear direction, whereupon a first image of the dentomaxillofacial area is created on said image receptor, said image being constituted about first intensity values that are proportional to the radiation with said first spectrum transmitted through said dentomaxillofacial area; returning said carrier and said X-ray beam after said first time moving thereof into said start position; providing an X-ray beam having a second radiation spectrum and the flat cross-sectional form towards said predetermined dentomaxillofacial area of the patient; utilizing said image receptor arranged in said carrier outside the head of the patient; while radiating said image receptor with said X-ray beam: moving for the second time said X-ray beam and said carrier with the inserted image receptor from said start position in said first rotational or linear direction, whereupon a second image of the same dentomaxillofacial area is created on said image receptor, said image being constituted about second intensity values that are proportional to the radiation with said second spectrum transmitted through said dentomaxillofacial area; subtracting said first intensity values and said second intensity values from each other, whereupon a resultant image is formed; and providing the resultant image as such or after processing for further use.

These methods can be utilized using a single CCD or CMOS cell as the image receptor. Alternatively these methods can be utilized using a single photographic film or stimulable memory plate as the image receptor. There is no need to have special image receptor with double receptor units. The two different radiation spectra are attained by positioning various metallic X-ray filters and/or operating without a metallic filter in said X-ray beam and/or changing the X-ray generating voltage.

Dual radiation spectrum scanning and subtraction system, i.e. using two different radiation spectra together with linear or panoramic scanning, where the movement speed of the projection of the object on the receptor is the movement speed of the receptor, for attaining two temporally separate images, followed by image data subtraction effectively decreases the noise generated by the porous bone material filled with water containing tissue and effectively decrease the effect of soft and hard tissue outside the dentomaxillofacial zone of interest. It is also much more easier to make difference between different types of tissues and detect changes in various tissues present in dentomaxillofacial area of interest.

BRIEF DESCRIPTION OF THE DRAWINGS

The foregoing summary, and the following detailed description of the preferred embodiments of the present invention, will be better understood when read in conjunction with the accompanying drawings, in which:

FIGS. 1A and 1B represent the first embodiment of the invention to expose the first image and the second image of a dentomaxillofacial area with different radiation spectra using a panoramic scanning X-ray apparatus and a CCD- or CMOS receptor, whereupon the moving directions for the two images are opposite, seen in direction perpendicular to the moving directions.

FIGS. 2A and 2B represent the second embodiment of the invention to expose the first image and the second image of a dentomaxillofacial area with different radiation spectra using a panoramic scanning X-ray apparatus and a CCD- or CMOS receptor, whereupon the moving directions for the two images are same, in the same view as in FIGS. 1A–1B.

FIGS. 3A and 3B represent the third embodiment of the invention to expose the first image and the second image of a dentomaxillofacial area with different radiation spectra using a panoramic scanning X-ray apparatus and a film or stimulable memory plate receptor, whereupon the moving directions for the two images are same and the images are exposed side by side on the receptor, in the same view as in FIGS. 1A–2B.

FIGS. 4A and 4B represent the fourth embodiment of the invention to expose the first image and the second image of a dentomaxillofacial area with different radiation spectra using a panoramic scanning X-ray apparatus and a film or stimulable memory plate receptor, thereupon the moving directions for the two images are opposite and the images are exposed on top of each other on the receptor, in the same view as in FIGS. 1A–3B.

FIGS. 5A and 5B represent the fifth embodiment of the invention to expose the first image and the second image of a dentomaxillofacial area with different radiation spectra using a linear scanning X-ray apparatus and a film or stimulable memory plate receptor. In FIG. 5A the moving directions of the X-ray source and the receptor is same but the speeds of the X-ray source and the receptor are different, and in FIG. 5B the moving directions of the X-ray source and the receptor are opposite; seen in the same direction as in FIGS. 1A–4B.

FIGS. 6 and 7 represent a single film or stimulable memory plate receptor, on which the first and second images according to the invention are exposed side by side in the direction of the movements, and on top of each other perpendicularly to the direction of the movements, respectively; seen perpendicular to the surface of the receptor.

FIG. 8 represent schematically the strip like CCD or CMOS receptor useful for the invention and the flat X-ray beam, which is hitting the receptor after passing through the dentomaxillofacial object.

DETAILED DESCRIPTION OF THE PREFERRED EMBODIMENTS

Figure 10:
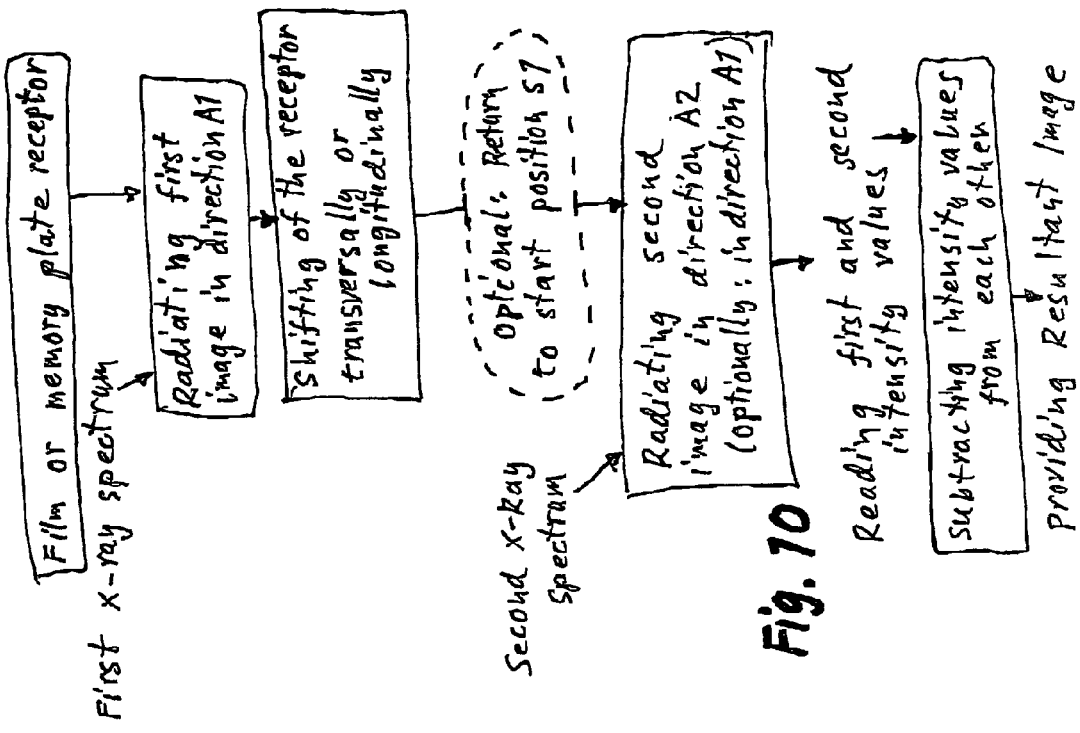
FIGS. 9 and 10 represent the main steps for performing the methods according to the invention when using CCD or CMOS receptor or using film or stimulable memory plate receptor.
Figure 9:
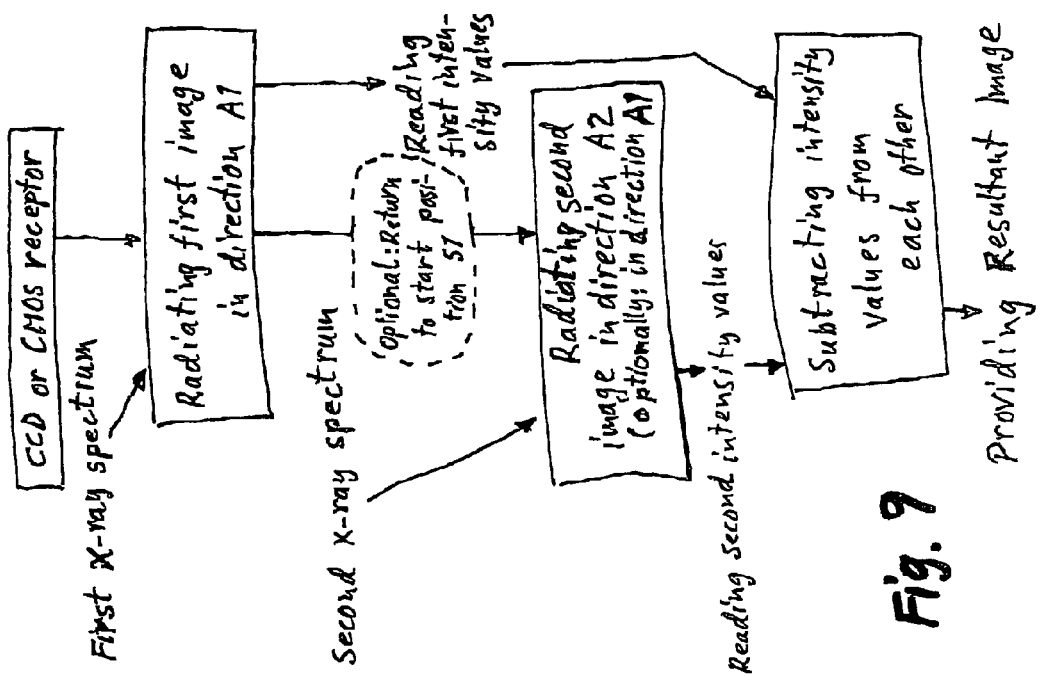

The basic parts of the known panoramic scanning X-ray apparatus and the known linear scanning apparatus comprise among other things a power source 5, which have means for altering at least the voltage kV fed to the X-ray tube, an X-ray tube 6, and a beam limiting device or collimator 4 having a narrow slit 16, whose length is perpendicular to the moving directions of the X-ray tube and the image receptor—in the FIGS. 1A to 5B perpendicular to the plane of the drawings, in front of the X-ray tube 6. From his X-ray source 10 an X-ray beam 15 having a flat cross-sectional form is directed during exposures through the object 13 onto the image receptor 8. The flat form of the X-ray beam 15 is shown in FIGS. 6 to 8, whereupon the beam width $W_B$ of the X-ray beam in the moving directions A1, A2 smaller than the image width $W_I$ is also visible, as well as the beam height $H_B$ perpendicular to the plane of the movements A1, A2. The image receptor 8 is arranged in a carrier 7, and positioned outside the head of the patient P so that the image receptor 8 transversal to the X-ray flat beam 15, typically perpendicular to the X-ray beam 15. In the panoramic scanning X-ray apparatus the carrier of the image receptor 8 and the X-ray tube 6 with the collimator 4 with the slit are interconnected by a common arm structure, not shown in the drawing. In the linear scanning apparatus the carrier of the image receptor 8 and the X-ray tube 6 with the collimator 4 with the slit are interconnected by a mechanical or electronic linear transfer mechanism, not shown in the drawing. The image receptor 8 may be a film 8b or a stimulable memory plate 8b, as shown in FIGS. 3A to 5B, or a CCD or CMOS cell 8a, as shown in FIGS. 1A to 2B, or any other known or new image-recording element, which is applicable to the purpose. During imaging, i.e. during exposures, the X-ray tube 6 and the carrier with the image receptor of the panoramic scanning X-ray apparatus turn around a common rotational axis 9, which can be stationary in a permanent position, or move along a linear or curved path. Depending on the type of the image receptor—line detector or large area detector—the receptor is either kept stationary in the carrier or is moved in the same or opposite direction as the linear or rotational movement of the carrier. During imaging, i.e. during exposures, the X-ray tube 6 and the carrier with the image receptor of the linear scanning X-ray apparatus move in respect to each other either the same or opposite direction, but typically parallel to each other. In both cases, i.e. panoramic and linear scanning the moving speed of the image receptor is matched with the moving speed of the X-ray tube so that sharp image is formed from the object zone, but any material in front of and behind of this zone is blurred by the movements. The object zone of interest, i.e. the predetermined dentomaxillofacial area Q of a patient, is inside and/or around the virtual or effective focal point formed by the mutual movements of the image receptor and the X-ray tube. The virtual or effective focal point is formed in place, from where the distances of the X-ray tube and the receptor are proportional to their velocities in directions perpendicular to the distances. By a proper design this virtual or effective focal point can be arranged to follow e.g. the form of the jaw or other zone configuration. These kind of panoramic or linear scanning X-ray apparatuses are traditionally used for imaging of the whole dentomaxillofacial region of the patient, like the whole jaw or all teeth from end to end. The panoramic and linear scanning apparatuses are known as such, and accordingly, are not explained in detail.

As can be understood, in the context of the invention the panoramic and linear scanning apparatuses are analogous to each other, because the essential feature that the receptor 8, 8a, 8b and the X-ray source 10 move in directions perpendicular the flat X-ray beam 15 is the same for both cases. It is secondary that the forms of movement paths are circular in the panoramic scanning imaging and linear in the linear scanning imaging. In the following text the same angular speed apply both panoramic scanning and linear scanning, whereupon the angle is around the virtual or effective focal point. The linear or circular velocities can be greatly different. For the purpose of the invention the images are not exposed e.g. from the whole length of the jaw of the patient, but in the invention such a short portion of the possible zone length is included in the image that risk for patient movement between the images is negligible. If the exposure time and so also the time difference between the exposures is a few seconds only, the errors caused by patient movements are normally low enough. In practice it is predetermined a dentomaxillofacial area Q that has a length in the jaw direction of the patient that is only a fraction of the whole jaw length. For his purpose the images are formed e.g. over a portion that is at maximum 30% of the jaw length, but typically about 20% length. For panoramic imaging this means that rotations are performed over an image angle at maximum 30° to attain the resultant image over a fraction of the jaw length of the patient. Respectively a shorter portion of the jaw length is predetermined for linear scanning, too, where the flat beam is substantially perpendicular to the jaw, to attain the resultant image over a fraction of the jaw length of the patient Both in the panoramic scanning imaging and in the linear scanning imaging the image receptor 8, 8a, 8b is radiated by the flat X-ray beam 15, which passes through the dentomaxillofacial area Q of interest for the first time, while moving the X-ray beam 15 and the carrier 7 with the inserted image receptor 8, 8a, 8b in the first rotational direction A1 or in the first linear direction A1. For this first radiating of the image receptor the flat X-ray bear 15 has the first radiation spectrum. When doing this, the first image of the intended dentomaxillofacial area Q is created on the image receptor. The first image is constituted about first intensity values that are proportional to that portion of the X-ray radiation, which has the first spectrum, and which has transmitted through this dentomaxillofacial area. In case of the CCD or CMOS cell 8a type image receptors the first intensity values forming the first image are typically read or received from the image receptor during the continuing exposure, e.g. each row R of pixels in the receptor 8a is read shortly after they have been exposed by the X-ray. The intensity values read/received in this way are saved in a memory in a digital processing unit. The receptor is erased after reading so as to make it ready for further receipt of X-ray radiation. In case of photographic film 8b or stimulable memory plate 8b type image receptors the first intensity values forming the first image are recorded in the image receptor inherent to these kinds of receptors.

After the first image of the dentomaxillofacial area Q of interest is totally exposed, The spectrum of the flat X-ray beam 15 is changed to be the second radiation spectrum followed by radiating the same image receptor 8, 8a, 8b by this altered X-ray beam, which also passes through the dentomaxillofacial area Q of interest now for the second time. During this moving the X-ray flat beam 15 and the carrier 7 with The inserted image receptor 8, 8a, 8b are moved in the second rotational direction A2 or in the second linear direction A2. These second directions A2 are opposite to the first directions A1. When doing this, the second image of the intended dentomaxillofacial area Q is created on the image receptor. The second image is constituted about second intensity values that are proportional to that portion of the X-ray radiation, which has the second spectrum, and which has transmitted through this dentomaxillofacial area Q. Again in case of the CCD or CMOS cell 8a type image receptors the second intensity values forming the second image are typically read or received from the image receptor during the continuing exposure, e.g. each row R of pixels in the receptor 8a is read shortly after their exposure by the X-ray. The intensity values read/received in this way are saved in a memory or forwarded directly to further processing in the digital processing unit. In case of photographic film 8b or stimulable memory plate 8b type image receptors the second intensity values forming the second image are recorded in the image receptor 8 according to the properties inherent to these kind of receptors, but in different place than the first image. Now, when it is question about films or memory plates 8b, both the first intensity values of the first image are read from an upper or lower half, or from left or right half of the image receptor to the digital processing unit, and the second intensity values of the second image from the lower or upper half, or the right or left half respectively of said image receptor to the digital processing unit. This is in principle normal film scanning or normal memory plate scanning, but now there are two images from the same dentomaxillofacial area Q with different information caused by different X-ray spectra used. The use of CCD or CMOS cell 8a type image receptors and the use of films or memory plates 8b are in this respect analogous to each other, the difference being the point of time for data reading/scanning. From films or memory plates the intensity values of both images are read by scanning after both images are exposed, but from CCD or CMOS cells the intensity values of both images are read by scanning during the exposures. In case of CCD or CMOS cells the scanning is directly from flat X-ray beam 15, but in case of films or memory plates there is the recording on these films or memory plates before the scanning.

Finally, the first intensity values and the second intensity values are subtracted from each other, whereupon a resultant image is formed. This subtraction is made in a digital processing unit like a computer, not shown in the figures. The resultant image attained can be provided as such or after additional processing for further use. These embodiments of the inventive system, where the image receptor and the X-ray source are moved in the first direction for the first image, and in the opposite second direction for the second image, are shown in FIGS. 1A, 1B, 4A, 4B and marked by unbroken and dashed arrows in FIGS. 5A and 5B. Concerning images the intensity values shall be understand to correspond density values of photographic material, though CCD and CMOS cells as well as stimulable memory plates do not have real densities, but electrical voltage values and latent information values that can be understood, handled and processed like densities.

Other embodiments of the inventive system, where the image receptor and the X-ray source are moved in the first direction for the first image, and in the same first direction for the second image, are shown in FIGS. 2A, 2B, 3A, 3B and marked by unbroken arrows in FIGS. 5A and 5B. Both in the panoramic scanning imaging and in the linear scanning imaging the image receptor 8, 8a, 8b is radiated by the flat X-ray beam 15, which passes through the dentomaxillofacial area Q of interest for the first time, while moving the X-ray beam 15 and the carrier 7 with the inserted image receptor 8, 8a, 8b from a start position S1 in the first rotational direction A1 or in the first linear direction A1. For this first radiating of the image receptor the flat X-ray beam 15 has the first radiation spectrum. When doing this, the first image of the intended dentomaxillofacial area Q is created on the image receptor. Deviating from the first embodiments the carrier and the X-ray beam are returned after this first time moving thereof into the start position S1. After the first image of the dentomaxillofacial area Q of interest is totally exposed, the spectrum of the flat X-ray beam 15 is changed to be the second radiation spectrum followed by radiating the same image receptor 8, 8a, 8b by this altered X-ray beam, which also passes through the dentomaxillofacial area Q of interest now for the second time. During this moving the X-ray beam 15 and the carrier 7 with the inserted image receptor 8, 8a, 8b are moved from the mentioned start position S1 in the first rotational direction A1 or the first linear direction A1. When doing this, the second image of the intended dentomaxillofacial area Q is created on the image receptor. The second image is constituted about second intensity values that are proportional to that portion of the X-ray radiation, which has the second spectrum, and which has transmitted through this dentomaxillofacial area Q. All what is said about the exposing of CCD or CMOS cell 8a type image receptors and about exposing photographic film 8b or stimulable memory plate 8b type image receptors, and everything what is said about the reading from these different image receptors 8, 8a, 8b, and everything what is said about the scanning in the context of previous embodiments are valid for this system, too, as can be readily understood—movement direction does not affect behaviour of the receptors. Finally, the first intensity values and the second intensity values are subtracted from each other, whereupon a resultant image is formed. This subtraction is made in a digital processing unit like a computer, not shown in the figures. The resultant image attained can be provided as such or after additional processing for further use.

If the CCD or CMOS cell 8a the image receptor 8 is used the flat X-ray beam 15, the beam 15 and the carrier 7 with the image receptor are moved with the same angular speed, i.e. the image receptor 8 is not moved in respect to the carrier 7, whereupon the image receptor 8, 8a is permanently during exposure of the images in the flat X-ray beam 15, i.e. the beam and the receptor does not move in respect to each other, as shown in the FIGS. 1A to 2B. Because the beam 15 during this time of exposure however wipes over the predetermined area Q of the patient, this area Q is scanned by the flat beam, and the scanning result temporarily recorded by the receptor 8, 8a for subsequent reading thereof. The CCD or CMOS cell type image receptor has a sensor height $H_S$ at least equal with the projection height of the predetermined dentomaxillofacial area Q for the images, and typically a sensor width $W_S$ about the same order as the beam width $W_B$, whereupon it shall be kept in mind that the beam width can be different for different imaging tasks, in which the same apparatus is possibly used, the CCD or CMOS cell type image receptor has a plurality of sensitive pixels within its sensor height $H_S$, and may have in principle only one row R of sensitive pixels in its sensor width $W_S$, but for different reasons preferably several pixels in this direction, too. Anyway the sensor width $W_S$ is, just like the beam width $W_B$, substantially smaller than the projection length of the predetermined dentomaxillofacial area Q and smaller than the image width $W_I$. Accordingly, the CCD or CMOS cell 8a type image receptor 8 can be considered as a line sensor for scanning. The image receptor 8, 8a is erased preferably immediately after reading, but especially prior to radiating the second image. In this system the image data comprising intensity values that are proportional to the radiation received by the image receptor 8, 8a is stored in a memory or memories, from which they can be read and displayed if wanted, but normally the first image and the second image are not used without subtraction. It is intended that only the resultant image is displayed or otherwise forwarded for further use.

Alternatively, if the photographic film 8b or stimulable memory plate 8b type image receptor 8 is used the flat X-ray beam 15, the beam 15 and the carrier 7 with the image receptor are moved with the same angular speed, but the image receptor 8, 8b is also moved during exposure of the images in respect to the flat X-ray beam 15 in the carrier so that the flat beam 15 wipes over the image area on the film or memory plate at the same time it wipes over the predetermined area Q of the patient, this area Q is scanned by the flat beam. In this case the scanning result is recorded for a longer time by the receptor 8, 8a for subsequent reading thereof. The film records the images permanently, and the memory plates until the images are read in a separate reading apparatus. When for the first image the X-ray beam 15, i.e. the X-ray source 10, and the opposed carrier 7 are moved in the first rotational direction A1 the image receptor 8, 8b is simultaneously moved in the third direction B3 that is either same as the first rotational direction A1, as in FIG. 3A, or opposite to the first rotational direction A1, as in FIG. 4A. This way the flat beam scans over the image width $W_I$. If then for the second image the flat X-ray beam 15 and the opposed carrier 7 are moved in the mentioned first rotational direction A1 the image receptor 8, 8b is simultaneously moved in the fourth direction B4 that is either same as the first rotational direction A1, as shown by unbroken arrow in FIG. 3B, or opposite to the first rotational direction A1, as shown by the dashed arrow in FIG. 3B. Alternatively, if for the second image the flat X-ray beam 15, i.e. the X-ray source 10, and the opposed carrier 7 are moved in the second rotational direction A2, which is opposite to the first direction A1, and the image receptor 8, 8b is simultaneously moved in the fourth direction B4 that is either same as the second rotational direction A2, as shown by dashed arrow in FIG. 4B, or opposite to the first rotational direction A1, as shown by the unbroken arrow in FIG. 4B. Whether the third or fourth direction B3, B4 are the same or the opposite to the first and second directions A1, A2 depends on the position of the predetermined dentomaxillofacial area Q, if between the rotational axis vs. virtual focal point and the image receptor the direction is opposite, as in FIGS. 4A and 4B, if between the rotational axis vs. virtual focal point and the X-ray source the direction is the same, as in FIGS. 3A and 3B. The beam width $W_B$ is substantially smaller than the projection length of the predetermined dentomaxillofacial area Q and smaller than the image width $W_I$, but receptor 8, 8b has larger area than the first and/or the second image K1, K2. Preferably the photographic film 8b or stimulable memory plate 8b has area or size large enough that both the first image K1 and the second image K3 can be recorded on it either side by side, as shown in FIG. 6, or on top of each other, as shown in FIG. 7. In this alternative it is possible to talk about images K1 and K2 because they are existing as a physical entities with real borders at least in a latent form, not only in the form of a data file. In this context we want to point out that images in digital form in a data file are images as well as any concrete images in latent or visible form, because visible pictures can be displayed and/or printed from any of these. In principle it is possible the record the two images onto separate films 8b or memory plates 8b, but using a single or one photographic film 8b or stimulable memory plate 8b, on which both the first and the second image are recorded, is more practical, e.g. to avoid differences between receptors 8, 8b. Analogous movements are performed in the linear scanning systems, too, as can be understood from the unbroken and dashed arrow describing the moving directions shown in FIGS. 5A and 5B.

There are two ways how the same predetermined area Q of the patient can be scanned two times by the flat X-ray beam 15. As explained the area Q is scanned for the first time for receiving the first image thereof, and for the second time for receiving the second image thereof. All other imaging parameters for the first image and for the second image shall be identical except the spectra, whereupon the first X-ray spectrum for the first image and the second X-ray spectrum for the second image are different. The movement of the flat X-ray beam 15 and the carrier 7 for the first image is made in the first rotational or linear direction A1 beginning from a start position S1. The movement of the flat X-ray beam 15 and the carrier 7 for the first image in the first direction A1 is ended in an end position S2. The second image can then be started from the end position S2 of the first image and ended in the start position S1 of the first image, whereupon the second rotational or linear direction A2 for the second image is opposite to the first direction A1 of the first image, as shown in FIGS. 1A to 1B and 4A to 4B. Alternatively the flat X-ray beam 15 and the carrier 7 can be returned after the first image from the end position S2 of the first image into the original start position S1 of the first image, whereafter the second image is exposed starting from the start point S1 and ended in the end point S2, while moving the X-ray beam and the opposed carrier for the second time in the first rotational or linear direction A1, as shown in FIGS. 2A to 2B and 3A to 3B.

There are several ways how to attain positioning of the first and the second images on the single photographic film 8b or stimulable memory plate 8b so that they are side by side or on top of each other. One alternative is to move the image receptor 8, 8b vertically or transversally over the height $H_I$ of the images, e.g. by shifting the image receptor a distance Hh that is equal to the image height $H_I$ upwards, as shown in FIG. 7, or downwards after exposing the first image K1 and prior to radiating the second image K2. In a modification of this alternative at least a collimator 4 for attaining said flat X-ray beam is moved vertically or transversally over the height $H_I$ of the images, more precisely the collimator slit 16 is changed or altered together with a tilt of the rotational axis and a vertical movement of the object in respect to the flat beam 15, so that the first image K1 and the second image K2 are projected and exposed on top of each other. When utilized in the embodiment, in which the two images are exposed while moving the flat X-ray beam 15 and the carrier 7 in the opposite directions A1 and A2, the carrier and the X-ray beam are returned after the first imaging into start position S1 preferably simultaneously with the shifting of the image receptor 8, 8b. This way the interval between the first image and the second image is minimized. In this alternative the first intensity values of the first image are read from an upper or lower half of the image receptor to the digital processing, and the second intensity values of the second image are read from the lower or upper half respectively of said image receptor to the digital processing, as explained earlier in this text. Of course this vertical or transversal shifting, i.e. shifting in the direction of the beam height $H_B$ can also be used in the embodiment, where the flat X-ray beam 15 and the carrier 7 are moved in the same direction A1 for the first image and the second image. Another alternative is to move the image receptor 8, 8b horizontally or longitudinally over the width $W_I$ of the images, e.g. by shifting the image receptor in forward direction a small distance G that is more than zero, after exposing the first image K1 and prior to radiating the second image K2. This alternative is most practical in the embodiments, in which the flat X-ray beam 15 and the carrier 7 are moved in the same direction A1 for the first image and the second image. This shifting is preferably made when returning the carrier and the X-ray beam after first imaging into the original start position S1. This shift can be also applied also in the embodiments in which the two images are exposed while moving the flat X-ray beam 15 and the carrier 7 in the opposite directions A1 and A2 the first intensity values of the first image are then read from a right or left half of the image receptor to the digital processing, and the second intensity values of the second image are read from the left or right half respectively of the image receptor to the digital processing. Accordingly, here transversal means transversal to the moving directions A1, A2 and longitudinal means direction parallel the moving directions A1, A2.

The first radiation spectrum can be attained e.g. by positioning a first metallic filter 11 or no filter in the X-ray beam 15, and the second radiation spectrum is attained by positioning no filter or a second metallic filter 12 in the X-ray beam. At least aluminum, gadolinium and copper can be used as the metallic material of the metallic filters 11, 12, as is generally known. The first radiation spectrum can also be attained by using a first tube voltage kV1 and the second radiation spectrum by using a second tube voltage kV2, as is generally known. For attaining two different spectra two different filters 11 and 12, or no filter and some filter 11 or 12 can be used alone, as shown in FIGS. 3A to 3B and 1A to 1B respectively, or two different tube voltages kV1 and kV2 generating said X-ray beam can be used alone, as shown in FIGS. 2A to 2B, or filters 11 and 12 and no filter together with changed tube voltages kV1, kV2 can be used combined, as shown in FIGS. 4A to 4B. The two spectra are different when they have different wavelength distributions, i.e. substantially different radiation intensities in some wavelengths.

The invention claimed is:

1. A method for dentomaxillofacial X-ray imaging comprising:
    providing an X-ray beam having a first radiation spectrum and a flat cross-sectional form towards a predetermined dentomaxillofacial area of a patient;
    arranging an image receptor in a carrier positioned outside the head of a patient, said image receptor being transversal to said X-ray beam;
    while radiating said image receptor with said X-ray beam through said dentomaxillofacial area: moving said X-ray beam and said carrier with said image receptor in a first rotational or linear direction,
        whereupon a first image of the dentomaxillofacial area is created on said image receptor, said image being constituted about first intensity values that are proportional to the radiation with said first spectrum transmitted through said dentomaxillofacial area;
    providing an X-ray beam having a second radiation spectrum and the flat cross-sectional form towards said predetermined dentomaxillofacial area of the patient;
    utilizing said image receptor arranged in said carrier outside the head of the patient;
    while radiating said image receptor with said X-ray beam having a second radiation spectrum: moving said X-ray beam and said carrier with the image receptor in a second rotational or linear direction that is opposite to said first direction,
        whereupon a second image of the same dentomaxillofacial area is created on said image receptor, said image being constituted about second intensity values that are proportional to the radiation with said second spectrum transmitted through said dentomaxillofacial area;
    subtracting said first intensity values and said second intensity values from each other, whereupon a resultant image is formed; and
    providing the resultant image as such or after processing for further use.

2. A method according to claim 1, wherein said predetermined dentomaxillofacial area has a length in a jaw direction of the patient that is a fraction of the whole jaw length of the patient.

3. A method according to claim 1, wherein said moving in the rotational directions are performed over an image angle to a maximum of 30° to attain the resultant image over a fraction of the jaw length of the patient.

4. A method according to claim 1, wherein said moving in the linear directions are performed over a portion of the jaw, wherein said beams are substantially perpendicular to the jaw, to attain the resultant image over a fraction of the jaw length of the patient.

5. A method according to claim 1, further comprising:
    inserting a single CCD or CMOS cell type image receptor in said carrier;
    moving said X-ray beam having the first radiation spectrum and said carrier in the first rotational or linear direction with the same angular speed;
    receiving said first intensity values of the first image from said image receptor for digital processing;
    erasing said image receptor prior to radiating for said second image;
    moving said X-ray beam having the second radiation spectrum and said carrier in the second rotational or linear direction with the same angular speed; and
    receiving said second intensity values of the second image from said image receptor for said digital processing,
        for said subtracting of the first intensity values and the second intensity values from each other during said digital processing.

6. A method according to claim 5, wherein said first image and said second image of the same dentomaxillofacial area are created on substantially the same region of said single image receptor.

7. A method according to claim 1, further comprising starting said moving of said X-ray beam having the second radiation spectrum and said carrier in said second direction from a point where said moving of said X-ray beam having the first radiation spectrum and said carrier in said first direction has ended.

8. A method according to claim 1, further comprising:
    inserting a single photographic film or stimulable memory plate type image receptor in said carrier;
    while moving said X-ray beam having the first radiation spectrum and said carrier in the first rotational direction, simultaneously moving said image receptor in a third direction that is the same or opposite to said first rotational direction;
    shifting said image receptor or at least a collimator for attaining said flat X-ray beams transversally over a direction a height of said first image prior to radiating for said second image;
    while moving said X-ray beam having the second radiation spectrum and said carrier in the second rotational direction, simultaneously moving said image receptor in a fourth direction that is the same or opposite to said second rotational direction;
    reading said first intensity values of the first image from an upper or lower half of the image receptor for digital processing; and
    reading said second intensity values of the second image from the lower or upper half respectively of said image receptor for said digital processing,
        for said subtracting of the first intensity values and the second intensity values from each other during said digital processing.

9. A method according to claim 1, wherein said first radiation spectrum differs from said second radiation spectrum; whereupon said first radiation spectrum is attained by positioning a first metallic filter or no filter for said X-ray beam having the first radiation spectrum, and said second radiation spectrum is attained by positioning no filter or a second metallic filter for said X-ray beam having the second radiation spectrum.

10. A method according to claim 9, wherein said first and second metallic filter are composed of a metal selected from a group of metals including at least aluminum, gadolinium and copper.

11. A method according to claim 1, wherein said first radiation spectrum differs from said second radiation spectrum; and the difference is attained by changing voltages generating said X-ray beams.

12. A method for dentomaxillofacial X-ray imaging comprising:
    providing an X-ray beam having a first radiation spectrum and a flat cross-sectional form towards a predetermined dentomaxillofacial area of a patient;

arranging an image receptor in a carrier positioned outside the head of a patient, said image receptor being transversal to said X-ray beam;

while radiating said image receptor with said X-ray beam, moving for a first time said X-ray beam and said carrier with the image receptor from a start position in a first rotational or linear direction, whereupon a first image of the dentomaxillofacial area is created on said image receptor, said image being constituted about first intensity values that are proportional to the radiation with said first spectrum transmitted through said dentomaxillofacial area;

returning said carrier and said X-ray beam after the first time moving thereof into said start position;

providing an X-ray beam having a second radiation spectrum and the flat cross-sectional form towards said predetermined dentomaxillofacial area of the patient;

utilizing said image receptor arranged in said carrier outside the head of the patient;

while radiating said image receptor with said X-ray beam having the second radiation spectrum: moving for a second time said X-ray beam having the second radiation spectrum and said carrier with the image receptor from said start position in said first rotational or linear direction, whereupon a second image of the same dentomaxillofacial area is created on said image receptor, said image being constituted about second intensity values that are proportional to the radiation with said second spectrum transmitted through said dentomaxillofacial area;

subtracting said first intensity values and said second intensity values from each other, whereupon a resultant image is formed; and providing the resultant image as such or after processing for further use.

13. A method according to claim 12, wherein said predetermined dentomaxillofacial area has a length in a jaw direction of the patient that is a fraction of the whole jaw length of the patient.

14. A method according to claim 12, wherein the rotating is performed over an image angle to a maximum 30° to attain the resultant image over a fraction of a jaw length of the patient.

15. A method according to claim 12, wherein said moving in the linear directions are performed over a portion of the jaw, where said beams are substantially perpendicular to the jaw, to attain the resultant image over a fraction of the jaw length of the patient.

16. A method according to claim 12, further comprising:
inserting a single CCD or CMOS cell type image receptor in said carrier;
moving said X-ray beam having the first radiation spectrum and said carrier for the first time in the first rotational or linear direction with the same angular speed;
receiving said first intensity values of the first image from said image receptor for digital processing;
erasing said image receptor prior to radiating for said second image;
after returning said carrier and X-ray source generating said X-ray beam having the first radiation spectrum into said start position, moving said X-ray beam having the second radiation spectrum and said carrier for the second time in the first rotational or linear direction with the same angular speed; and receiving said second intensity values of the second image from said image receptor for said digital processing, for said subtracting of the first intensity values and the second intensity values from each other during said digital processing.

17. A method according to claim 16, wherein said first image and said second image of the same dentomaxillofacial area are created on substantially the same region of said single image receptor.

18. A method according to claim 12, further comprising:
inserting a single photographic film or stimulable memory plate type image receptor in said carrier;
while moving said X-ray beam having the first radiation spectrum and said carrier for the first time in the first rotational direction, simultaneously moving said image receptor in a third direction that is the same or opposite to said first rotational direction;
shifting said image receptor or at least a collimator for attaining said flat X-ray beam transversally over a direction of a height of said first image prior to radiating for said second image after returning said carrier and an X-ray source generating said X-ray beam having the first radiation spectrum into said start position;
while rotating said X-ray beam having the first radiation spectrum and said carrier for the second time in the first rotational direction, simultaneously moving said image receptor in a fourth direction that is the same or opposite to said first rotational direction;
reading said first intensity values of the first image from an upper or lower half of the image receptor for digital processing; and
reading said second intensity values of the second image from the lower or upper half respectively of said image receptor for said digital processing,
for said subtracting of the first intensity values and the second intensity values from each other during said digital processing.

19. A method according to claim 12, wherein said first radiation spectrum differs from said second radiation spectrum; whereupon said first radiation spectrum is attained by positioning a first metallic filter or no filter for said X-ray beam having the first radiation spectrum, and said second radiation spectrum is attained by positioning no filter or a second metallic filter for said X-ray beam having the second radiation spectrum.

20. A method according to claim 12, wherein said first and second metallic filters are composed of a metal selected from a group of metals including at least aluminum, gadolinium, and copper.

21. A method according to claim 12, wherein said first radiation spectrum differs from said second radiation spectrum; and the difference is attained by changing voltages generating said X-ray beams.

22. A method according to claim 12, further comprising:
inserting a single photographic film or stimulable memory plate type image receptor in said carrier;
while moving said X-ray beam having the first radiation spectrum and said carrier for the first time in the first rotational direction, simultaneously moving said image receptor in a third direction that is the same or opposite to said first rotational direction;
shifting said image receptor longitudinally from a position for said first image prior to radiating for said second image after returning said carrier and an X-ray source generating said X-ray beam having the first radiation spectrum into said start position;

while rotating said X-ray beam having the second radiation spectrum and said carrier for the second time in the first rotational direction, simultaneously moving said image receptor in a fourth direction that is the same or opposite to said first rotational direction;

reading said first intensity values of the first image from a right or left half of the image receptor for digital processing; and reading said second intensity values of the second image from the left or right half respectively of said image receptor for said digital processing, for said subtracting of the first intensity values and the second intensity values from each other during said digital processing.

* * * * *